United States Patent [19]

Kristiansen et al.

[11] Patent Number: 4,602,021

[45] Date of Patent: Jul. 22, 1986

[54] PHENYLBENZOYLUREAS USEFUL AS PESTICIDES

[75] Inventors: Odd Kristiansen, Möhlin; Jozef Drabek, Oberwil, both of Switzerland

[73] Assignee: Ciba-Geigy Corporation, Ardsley, N.Y.

[21] Appl. No.: 745,456

[22] Filed: Jun. 17, 1985

[30] Foreign Application Priority Data

Jun. 22, 1984 [CH] Switzerland ........................ 3030/84

May 31, 1985 [CH] Switzerland ........................ 2316/85

[51] Int. Cl.[4] .................. A01N 43/16; C07D 309/14; A01N 43/40

[52] U.S. Cl. .................................. 514/336; 514/459; 549/424; 546/268

[58] Field of Search ........................ 549/424; 546/268; 514/459, 336

[56] References Cited

U.S. PATENT DOCUMENTS 4,426,385 1/1984 Cain .................................. 546/268

*Primary Examiner*—Nicky Chan

*Attorney, Agent, or Firm*—Edward McC. Roberts; Kevin T. Mansfield

[57] ABSTRACT

The invention relates to novel substituted N-phenyl-N-tetrahydropyranyl-N'-benzoylureas of the formula

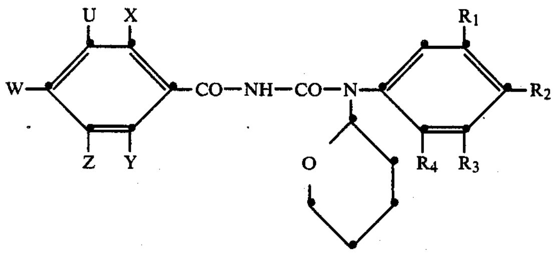

wherein $R_1$ is hydrogen, halogen, $C_1$–$C_6$alkyl, $C_1$–$C_3$haloalkyl containing 1 to 7 halogen atoms, $C_1$–$C_6$alkoxy, $C_1$–$C_6$alkylthio, $C_1$–$C_3$haloalkoxy containing 1 to 7 halogen atoms, nitro, cyano, ethynyl or one of the groups $-CO-OR_5$ or wherein $R_5$, $R_6$ and $R_7$ are $C_1$–$C_6$alkyl;

$R_2$, $R_3$ and $R_4$ are each independently hydrogen, halogen, $C_1$–$C_6$alkyl, $C_1$–$C_3$haloalkyl containing 1 to 7 halogen atoms, $C_1$–$C_6$alkoxy, $C_1$–$C_6$alkylthio, $C_1$–$C_3$haloalkoxy containing 1 to 7 halogen atoms, nitro, cyano, ethynyl or one of the groups $-CO-OR_5$ or wherein $R_5$, $R_6$ and $R_7$ are $C_1$–$C_6$alkyl,

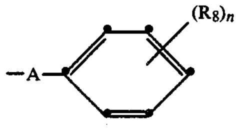

wherein —A— is —O— or —S—, $R_8$ is halogen, methyl, nitro, $CF_3$ or cyano and n is 0, 1, 2 or 3, or

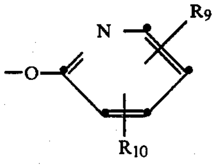

wherein each of $R_9$ and $R_{10}$ independently is hydrogen, chlorine, trifluoromethyl or an ethyl radical perhalogenated with fluorine and/or chlorine; and U, X, Y, Z and W are each independently hydrogen, halogen, $C_1$–$C_3$alkyl, $C_1$–$C_3$alkoxy or $C_1$–$C_3$alkylthio, to the preparation of these compounds and to compositions containing them for controlling insects and representatives of the order Acarina. The novel compounds exhibit larvicidal activity, especially against plant-destructive insects.

9 Claims, No Drawings

PHENYLBENZOYLUREAS USEFUL AS PESTICIDES

The present invention relates to novel N-phenyl-N-tetrahydropyranyl-N'-benzoylureas, to the preparation thereof and to the use thereof in pest control.

Accordingly, the invention relates to N-phenyl-N-tetrahydropyranyl-N'-benzoylureas of formula I

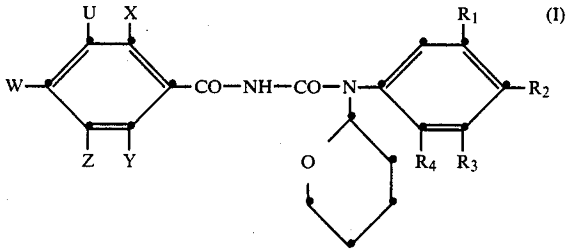
(I)

wherein $R_1$ is hydrogen, halogen, $C_1$-$C_6$alkyl, $C_1$-$C_3$haloalkyl containing 1 to 7 halogen atoms, $C_1$-$C_6$alkoxy, $C_1$-$C_6$alkylthio, $C_1$-$C_3$haloalkoxy containing 1 to 7 halogen atoms, nitro, cyano, ethynyl or one of the groups $-CO-OR_5$ or 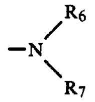

wherein $R_5$, $R_6$ and $R_7$ are $C_1$-$C_6$alkyl;

$R_2$ $R_3$ and $R_4$ are each independently hydrogen, halogen, $C_1$-$C_6$alkyl, $C_1$-$C_3$haloalkyl containing 1 to 7 halogen atoms, $C_1$-$C_6$alkoxy, $C_1$-$C_6$alkylthio, $C_1$-$C_3$haloalkoxy containing 1 to 7 halogen atoms, nitro, cyano, ethynyl or one of the groups $-CO-OR_5$ or 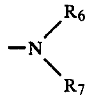

wherein $R_5$, $R_6$ and $R_7$ are $C_1$-$C_6$alkyl,

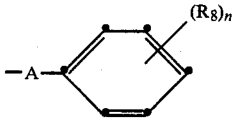

wherein —A— is —O— or —S—, $R_8$ is halogen, methyl, nitro, $CF_3$ or cyano and n is 0, 1, 2 or 3, or

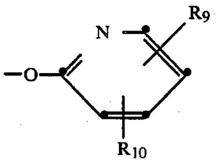

wherein each of $R_9$ and $R_{10}$ independently is hydrogen, chlorine, trifluoromethyl or an ethyl radical perhalogenated with fluorine and/or chlorine; and U, X, Y, Z and W are each independently hydrogen, halogen, $C_1$-$C_3$alkyl, $C_1$-$C_3$alkoxy or $C_1$-$C_3$alkylthio.

Preferred compounds of formula I of the present invention are such compounds wherein $R_1$ is hydrogen, fluorine, chlorine, trifluoromethyl, $-CO-OCH_3$ or $-CO-OC_2H_5$;

$R_2$ is hydrogen, fluorine, chlorine, $C_1$-$C_2$haloalkyl containing 1 to 5 chlorine and/or fluorine atoms, $C_1$-$C_2$haloalkoxy containing 1 to 5 chlorine and/or fluorine atoms, cyano, ethynyl or one of the groups

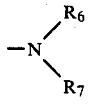

wherein $R_6$ and $R_7$ are $C_1$-$C_3$alkyl,

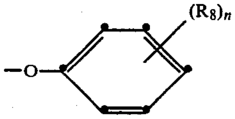

wherein $R_8$ is fluorine or chlorine and n is 0, 1 or 2,

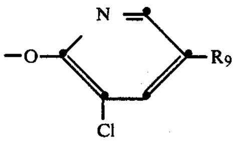

wherein $R_9$ is hydrogen, chlorine, trifluoromethyl or $-CF_2-CFCl_2$,

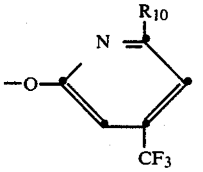

wherein $R_{10}$ is hydrogen or chlorine;

$R_3$ and $R_4$ are each independently hydrogen, halogen, trifluoromethyl, methyl or ethyl;

U Z and W are hydrogen;

X is fluorine, chlorine, bromine or $C_1$-$C_3$alkyl; and

Y is hydrogen, fluorine, chlorine, bromine or $C_1$-$C_3$alkyl.

Particularly preferred compounds of formula I are such compounds wherein $R_1$ is hydrogen, fluorine, chlorine or $-CO-OCH_3$;

$R_2$ is hydrogen, fluorine, chlorine, trifluoromethyl, ethynyl, trifluoromethoxy, $-O-CF_2-CF_2Cl$, $-O-CF_2-CHF_2$, $-O-CF_2-CFCl_2$ or one of the groups

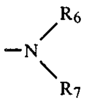

wherein $R_6$ is methyl and $R_7$ is $C_1$-$C_3$alkyl,

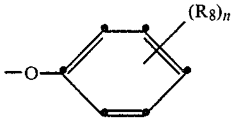

wherein $R_8$ is hydrogen, fluorine or chlorine,

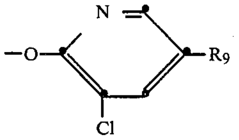

wherein $R_9$ is trifluoromethyl or —$CF_2$—$CFCl_2$, or

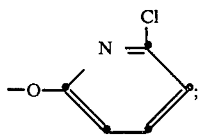

$R_3$ and $R_4$ are each independently hydrogen, fluorine, chlorine, trifluoromethyl or methyl;
U, Z and W are hydrogen;
X is fluorine or chlorine; and
Y is hydrogen, fluorine or chlorine; as well as such compounds of formula I wherein
$R_1$ is chlorine or trifluoromethyl;
$R_2$ is chlorine, trifluoromethyl, trifluoromethoxy, —O—$CF_2$—$CHF_2$ or the group

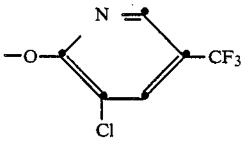

$R_3$ is hydrogen, chlorine or —CO—$OCH_3$;
$R_4$ is hydrogen;
U, Z and W are hydrogen;
X is fluorine or chlorine; and
Y is hydrogen or fluorine.

Depending on the number of carbon atoms indicated, the term alkyl within the scope of the present invention will be understood as meaning straight chain and branched alkyl radicals, for example the following groups: methyl, ethyl, propyl, butyl and pentyl, and the isomers thereof, e.g. isopropyl, isobutyl, tert-butyl, isopentyl etc. Halogen will be understood as meaning fluorine, chlorine, bromine and iodine, preferably fluorine and chlorine.

The compounds of formula I can be prepared by methods analogous to ones known per se. Thus, for example, a compound of formula I can be obtained by reacting a compound of formula II

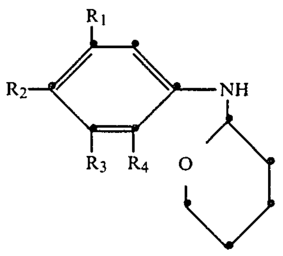

(II)

with a compound of formula III

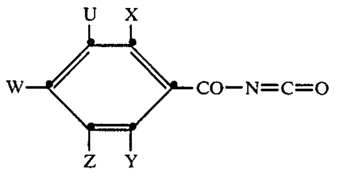

(III)

in which formulae II and III the radicals $R_1$, $R_2$, $R_3$, $R_4$, U, X, Y, Z and W are as defined above.

The aforementioned process can preferably be carried out under normal pressure and in the presence of an organic solvent or diluent. Examples of suitable solvents or diluents are ethers and ethereal compounds such as diethyl ether, dipropyl ether, dibutyl ether, dioxane, dimethoxyethane and tetrahydrofuran; N,N-alkylated carboxylic acid amides; aliphatic, aromatic and halogenated hydrocarbons, in particular benzene, toluene, xylene, chloroform, metylene chloride, carbon tetrachloride and chlorobenzene; nitriles such as acetonitrile or propionitrile; dimethylsulfoxide; and ketones such as acetone, methyl ethyl ketone, methyl isopropyl ketone and methyl isobutyl ketone. The process is generally carried out at a temperature in the range from −10° to 100° C., preferably from 15° to 25° C., and, if appropriate, in the presence of an organic base, e.g. triethylamine. It is most preferred to carry out the process at room temperature.

The N-tetrahydropyranylanilines of formula II employed as starting materials in the above process can be prepared according to the process described in J. Org. Chem. USSR 2034 (1976) by reacting corresponding anilines of formula IV

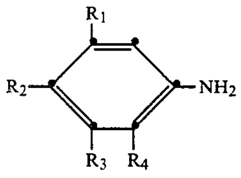

(IV)

with 5-hydroxypentanal. Said anilines of formula IV are known (q.v. e.g. DE-OS Nos. 3241138A1 and 3240975A1).

It is known that N-phenyl-N'-benzoylureas containing substituents of varying kind at both the phenyl and the benzoyl moiety possess insecticidal properties (q.v. e.g. British patent specification No. 1 324 293). Compared with these known phenylbenzoylureas, the compounds of the present invention are novel N-phenyl-N-(tetrahydropyran-2″-yl)-N′-benzoylureas, the specific structure of which is characterised in particular by the tetrahydropyranyl group attached to the N atom. Surprisingly, these novel compounds exhibit excellent activity as pesticides, in particular for plant protection. A particular advantage of the compounds of formula I of the present invention is their very low mammalian toxicity and that they are also well tolerated by plants.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families: Ioxididae, Argasidae, Tetranychidae and Dermanyssidae.

In addition to their action against flies, e.g. *Musca domestica,* and mosquito larvae, the compounds of formula I are also suitable for controlling plant-destructive feeding insects in ornamentals and crops of useful plants, especially in cotton (e.g. against *Spodoptera littoralis* and *Heliothis virescens*) and in fruit and vegetables (e.g. against *Laspeyresia pomonella, Leptinotarsa decemlineata* and *Epilachna varivestis*). The compounds of formula I have ovicidal and, in particular, larvicidal action against insects, especially against larvae of noxious feeding insects. If compounds of formula I are ingested by adult insect stages with the feed, then a diminished oviposition and/or reduced hatching rate is observed in many insects, especially in Coleoptera, e.g. *Anthonomus grandis.*

The compounds of formula I can also be used for controlling ectoparasites, e.g. ticks and flies such as *Lucilia sericata,* in domestic animals and productive livestock, preferably e.g. by treating animals, cowsheds, barns, stables etc., and pastures.

The compounds of formula I are also suitable for controlling the following species of mites which attack crops of fruit and vegetables: *Tetranychus urticae, Tetranychus cinnabarinus, Panonychus ulmi, Broybia rubrioculus, Panonychus citri, Eriophyes piri, Eriophyes ribis, Eriophyes vitis, Tarsonemus pallidus, Phyllocoptes vitis* and *Phyllocoptruta oleivora.*

The good pesticidal activity of the compounds of formula I of the invention corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol-/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

FORMULATION EXAMPLES FOR SOLID ACTIVE INGREDIENTS OF FORMULA I OR COMBINATIONS THEREOF WITH OTHER INSECTICIDES OR ACARICIDES (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4-5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded, granulated and then dried in a stream of air.

| 5. Coated granulate | |
|---|---|
| compound of formula I or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 1

(a) Preparation of
3,5-dichloro-4-(3'-chloro-5'-trifluoromethylpyridyl-2'-oxy)-N-(tetrahydropyran-2''-yl)aniline A mixture of 17.8 g of 3,5-dichloro-4-(2'-chloro-5'-trifluoromethylpyridyl-2'-oxy)aniline and 5.3 g of 5-hydroxypentanal is stirred for 2 hours at 85° C. After cooling, the crude product obtained is taken up in chloroform and the resultant solution is dried over sodium sulfate and concentrated by evaporation. The residue is then taken up in hexane and the title compound of the formula

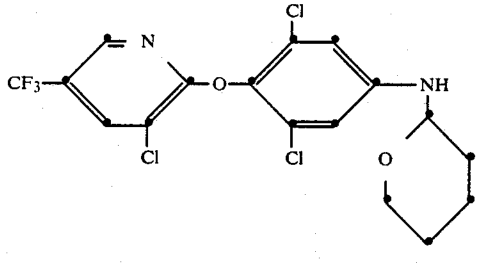

crystallises from this solution as white crystals with a melting point of 74°-76° C.

(b) Preparation of
N-[3,5-dichloro-4-(3'-chloro-5'-trifluoromethylpyridyl-2'-oxy)phenyl]-N-(tetrahydropyran-2''-yl)-N'-2-chlorobenzoyl urea A solution of 1.9 g of 2-chlorobenzoylisocyanate in 5 ml of diethyl ether is added dropwise to a solution of 4.4 g of the above aniline, prepared according to (a), in 40 ml of diethyl ether. The batch is stirred for two hours at room temperature and the crystallised reaction product is then isolated by filtration and washed with a small amount of diethyl ether, affording the title compound of the formula

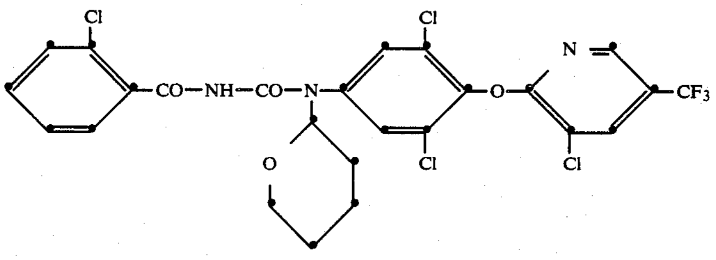

with a melting point of 152°-153° C. (compound No. 1).

The following compounds of formula I are prepared by procedures analogous to those described above:

| Compound No. | | m.p. [°C.] |
|---|---|---|
| 2 | 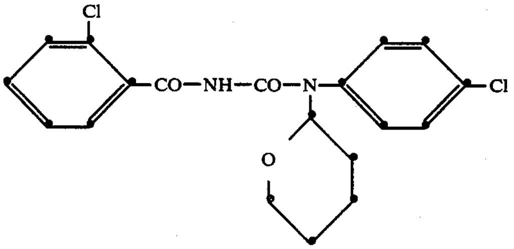 | 159-160 |

-continued
| Compound No. | | m.p. [°C.] |
|---|---|---|
| 3 | 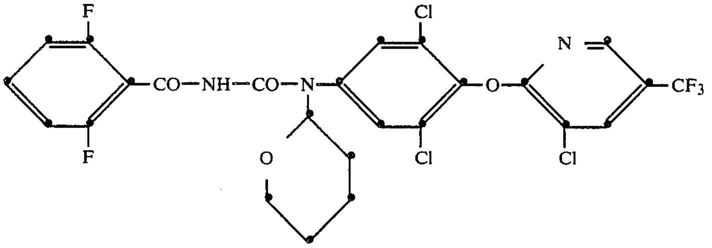 | 112-114 |
| 4 | 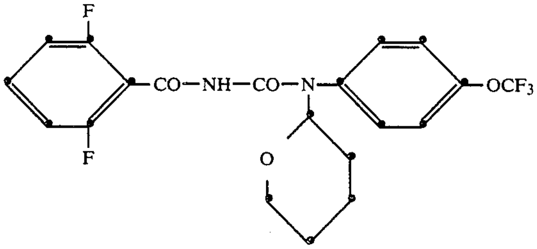 | 151-152 |
| 5 | 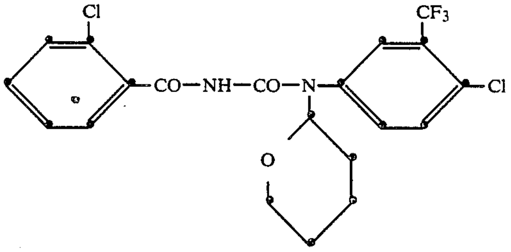 | 159-160 |
| 6 | 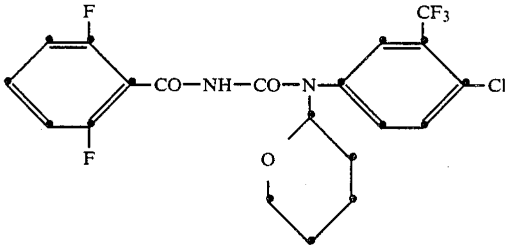 | 160-162 |
| 7 | 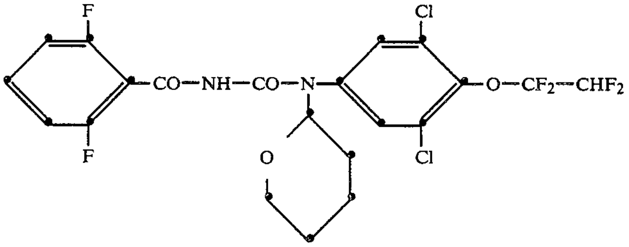 | 159-160 |
| 8 | 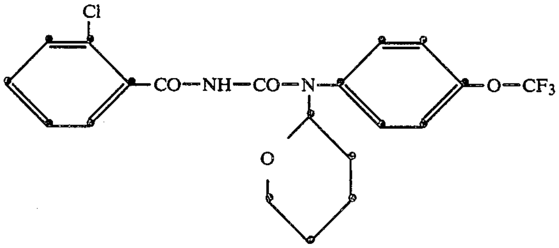 | 152-154 |

-continued
| Compound No. | | m.p. [°C.] |
|---|---|---|
| 9 | 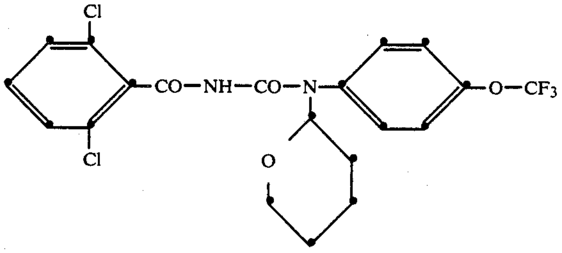 | 171–172 |
| 10 | 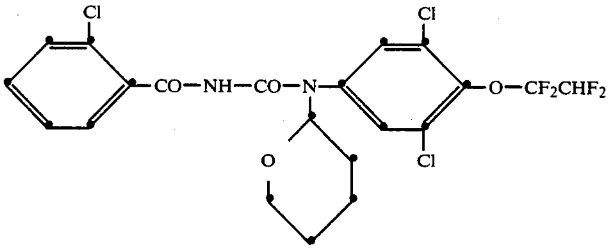 | 150–151 |
| 11 | 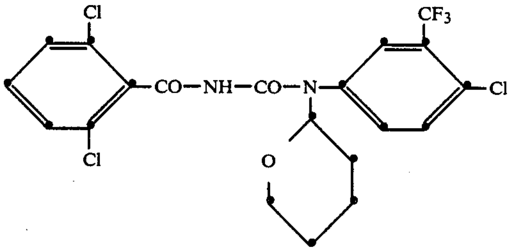 | 167–169 |
| 12 | 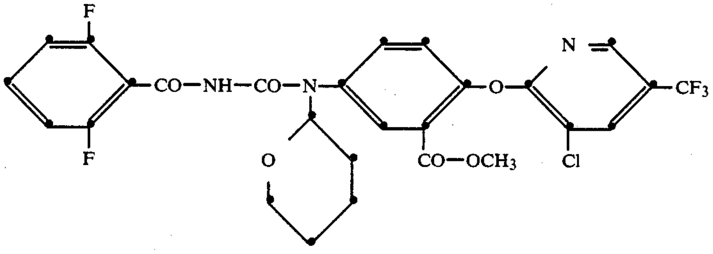 | 147–149 |
| 13 | 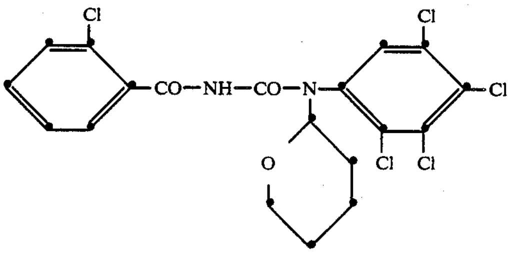 | 179–180 |
| 14 | 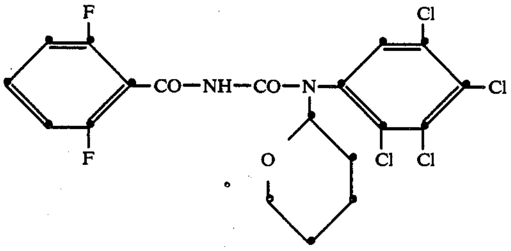 | 193–194 |

-continued
| Compound No. | | m.p. [°C.] |
|---|---|---|
| 15 | 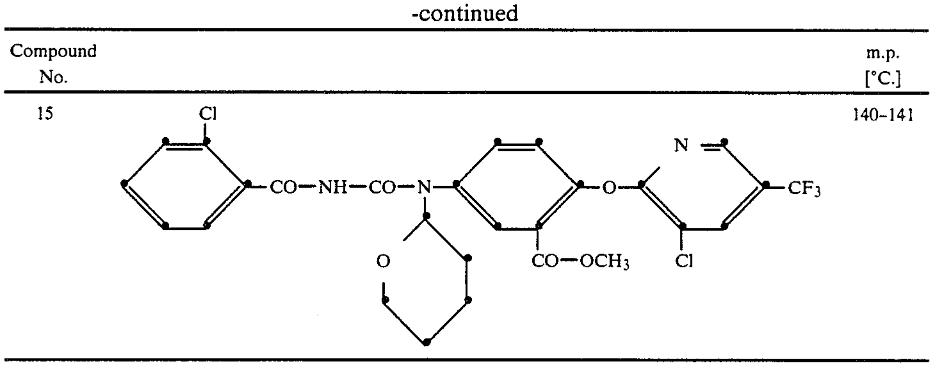 | 140-141 |
The following compounds can also be prepared in a manner corresponding to that described above:
| Compound No. | |
|---|---|
| 16 | 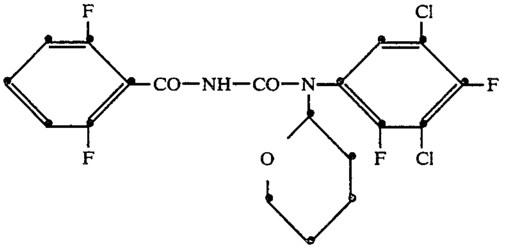 |
| 17 | 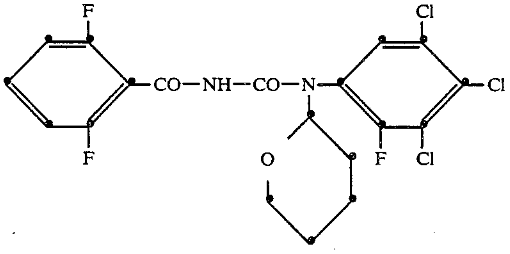 |
| 18 | 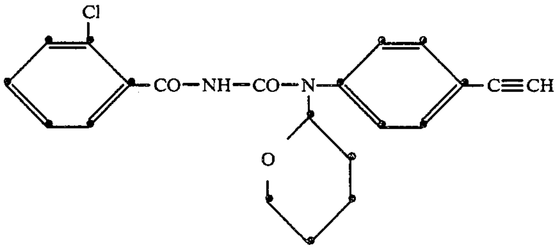 |
| 19 | 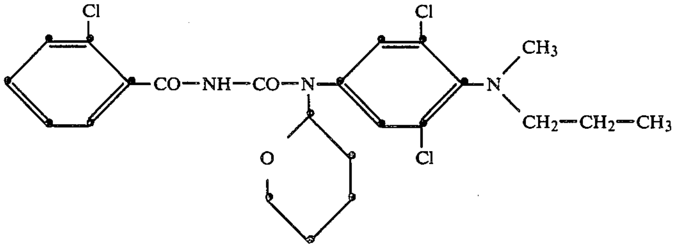 |

-continued

| Compound No. | |
|---|---|
| 20 | 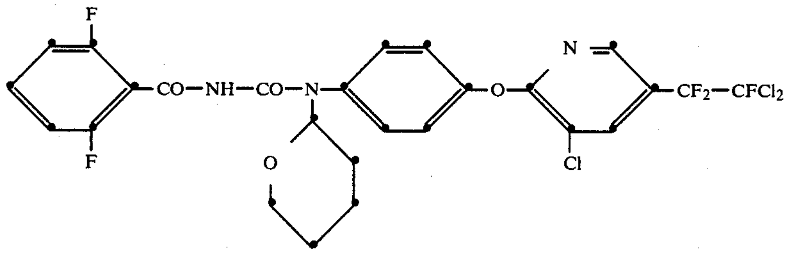 |
| 21 | 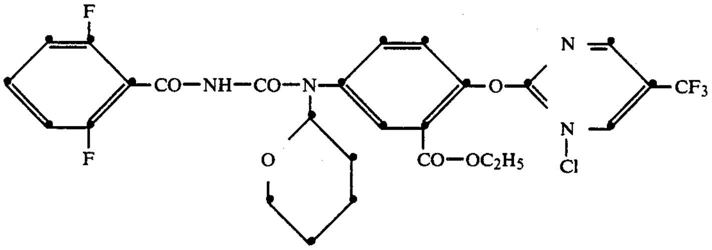 |

EXAMPLE 2

Action against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at one of its given concentrations. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Example 1 have good activity in this test.

EXAMPLE 3

Action against *Lucilia sericata*

1 ml of an aqueous formulation containing the test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. In this test, compounds of formula I according to Example 1 exhibit good activity against *Lucilia sericata.* The foregoing compounds 4 and 12 effect 100% kill against *Lucilia sericata* at a concentration of 50 ppm.

EXAMPLE 4

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 1, 2 and 5 days.

In this test, compounds of formula I according to Example 1 exhibit good activity against *Aedes aegypti.*

EXAMPLE 5

Insecticidal action against feeding insects

Cotton plants about 25 cm high, in pots, are sprayed with aqueous emulsions which contain the test compound in concentrations of 3 to 200 ppm. After the spray coating has dried, the cotton plants are populated with *Spodoptera littoralis* and *Heliothis virescens* larvae in the $L_3$-stage. The test is carried out at 24° C. and 60% relative humidity. The percentage mortality of the test insects is determined after 120 hours.

EXAMPLE 6

Action against *Epilachna varivestis*

*Phaseolus vulgaris* plants (dwarf beans) about 15-20 cm in height are sprayed with aqueous emulsion formulations of the test compound in concentrations of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

The compounds of formula I according to Example 1 exhibit good activity in this test.

EXAMPLE 7

Ovicidal action against *Heliothis virescens*

Corresponding amounts of a wettable powder formulation containing 25% by weight of the test compound are mixed with sufficient water to produce an aqueous emulsion with an active ingredient concentration of 800 ppm. One day-old egg deposits of Heliothis on cellophane are immersed in these emulsions for 3 minutes and then collected by suction on round filters. The treated deposits are placed in petri dishes and kept in the dark. The hatching rate in comparison with untreated controls is determined after 6 to 8 days. Evaluation is made to determine the minimum concentration of compound required to effect 100% kill of the eggs. In this test the compounds of formula I according to Example 1 exhibit good action.

EXAMPLE 8

Action against *Laspeyresia pomonella* (eggs)

Egg deposits of *Laspeyrasia pomonella* not more than 24 hours old are immersed on filter paper for 1 minute in an acetonic aqueous solution containing 800 ppm of the test compound.

After the solution has dried, the eggs are placed in petri dishes and kept at a temperature of 28° C. The percentage of larvae hatched from the treated eggs and the percentage mortality is evaluated after 6 days.

The compounds of formula I according to Example 1 exhibit good activity in this test.

EXAMPLE 9

Influence on the reproduction of *Anthonomus grandis*

*Anthonomus grandis* adults which are not more than 24 hours old after hatching are transferred in groups of 25 to barred cages. The cages are then immersed for 5 to 10 seconds in acetonic solutions containing 12.5 to 200 ppm of the test compound. When the beetles are dry, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

EXAMPLE 10

Acaricidal action 12 hours before the test for acaricidal action, *Phaseolus vulgaris* plants are infected with an infested piece of leaf from a mass culture of *Tetranychus urticae.* The treated plants infested with the mobile stages which have migrated to the plants are sprayed from a chromatography atomiser with emulsified test solutions each having an active ingredient concentration of 800 ppm so that the plants do not drip. A count of living and dead larvae, adults and eggs is made under a stereoscopic microscope after 2 days and again after 7 days. The result is expressed in percent. During the test run, the plants stand in greenhouse compartments at 25° C.

Compounds of formula I according to Example 1 exhibit good activity in the above test.

EXAMPLE 11

Action against *Anthonomus grandis* (adults)

Two cotton plants in the 6-leaf stage, in pots, are each sprayed with a wettable aqueous emulsion formulation containing the test compound in a concentration of 12.5 ppm. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of formula I according to Example 1 exhibit good activity in this test.

RESULTS OF BIOLOGICAL TESTS

The results of the biological tests carried out with the compounds of the invention in accordance with the foregoing Examples 5 and 9 are shown in the following table. Evaluation of the test in terms of percentage mortality is made using the following rating:

A: 80–100% mortality at a concentration of 3 ppm of the tested compound
B: 80–100% mortality at a concentration of 12.5 ppm of the tested compound
C: 80–100% mortality at a concentration of 50 ppm of the tested compound
D: 80–100% mortality at a concentration of 100 ppm of the tested compound
E: 80–100% mortality at a concentration of 200 ppm of the tested compound

| Compound No. | Pesticidal activity | | |
|---|---|---|---|
| | Spodoptera (Example 5) | Heliothis (Example 5) | Anthonomus (Example 9) |
| 1 | B | C | B |
| 3 | A | B | B |
| 4 | — | — | B |
| 5 | E | — | — |
| 6 | B | — | C |
| 7 | B | — | — |
| 8 | C | C | B |
| 10 | C | E | D |
| 12 | A | B | B |
| 13 | — | — | E |
| 15 | A | B | C |

What is claimed is:

1. A compound of formula I

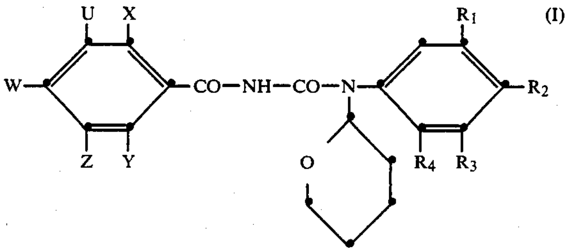
(I)

wherein $R_1$ is hydrogen, halogen, $C_1$–$C_6$alkyl, $C_1$–$C_3$haloalkyl containing 1 to 7 halogen atoms, $C_1$–$C_6$alkoxy, $C_1$–$C_6$alkylthio, $C_1$–$C_3$haloalkoxy containing 1 to 7 halogen atoms, nitro, cyano, ethynyl or one of the groups $-CO-OR_5$ or 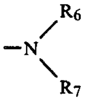

wherein $R_5$, $R_6$ and $R_7$ are $C_1$–$C_6$alkyl;

$R_2$, $R_3$ and $R_4$ are each independently hydrogen, halogen, $C_1$–$C_6$alkyl, $C_1$–$C_3$haloalkyl containing 1 to 7 halogen atoms, $C_1$–$C_6$alkoxy, $C_1$–$C_6$alkylthio, $C_1$–$C_3$haloalkoxy containing 1 to 7 halogen atoms, nitro, cyano, ethynyl or one of the groups $-CO-OR_5$ or 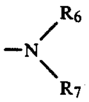

wherein $R_5$, $R_6$ and $R_7$ are $C_1$–$C_6$alkyl,

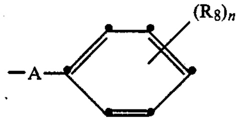

wherein —A— is —O— or —S—, $R_8$ is halogen, methyl, nitro, $CF_3$ or cyano and n is 0, 1, 2 or 3, or

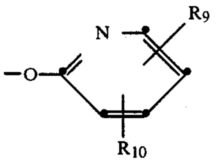

wherein each of $R_9$ and $R_{10}$ independently is hydrogen, chlorine, trifluoromethyl or an ethyl radical perhalogenated with fluorine and/or chlorine; and U, X, Y, Z and W are each independently hydrogen, halogen, $C_1$–$C_3$alkyl, $C_1$–$C_3$alkoxy or $C_1$–$C_3$alkylthio.

2. A compound of formula I according to claim 1, wherein $R_1$ is hydrogen, fluorine, chlorine, trifluoromethyl, $-CO-OCH_3$ or $-CO-OC_2H_5$;

$R_2$ is hydrogen, fluorine, chlorine, $C_1$–$C_2$haloalkyl containing 1 to 5 chlorine and/or fluorine atoms, $C_1$–$C_2$haloalkoxy containing 1 to 5 chlorine and/or fluorine atoms, cyano, ethynyl or one of the groups

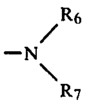

wherein $R_6$ and $R_7$ are $C_1$–$C_3$alkyl,

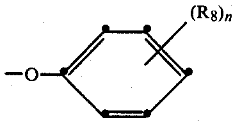

wherein $R_8$ is fluorine or chlorine and n is 0, 1 or 2,

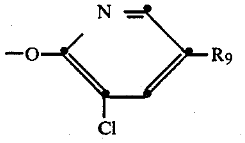

wherein $R_9$ is hydrogen, chlorine, trifluoromethyl, $-CF_2-CF_2Cl$ or $-CF_2-CFCl_2$,

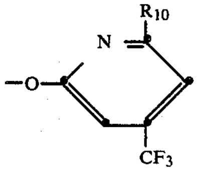

wherein $R_{10}$ is hydrogen or chlorine;

$R_3$ and $R_4$ are each independently hydrogen, halogen, trifluoromethyl, methyl or ethyl;

U, Z and W are hydrogen;

X is fluorine, chlorine, bromine or $C_1$–$C_3$alkyl; and

Y is hydrogen, fluorine, bromine or $C_1$–$C_3$alkyl.

3. A compound of formula I according to claim 1, wherein $R_1$ is hydrogen, fluorine, chlorine or $-CO-OCH_3$;

$R_2$ is hydrogen, fluorine, chlorine, trifluoromethyl, ethynyl, trifluoromethoxy, $-O-CF_2-CF_2Cl$, $-O-CF_2-CHF_2$, $-O-CF_2-CFCl_2$ or one of the groups

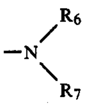

wherein $R_6$ is methyl and $R_7$ is $C_1$–$C_3$alkyl,

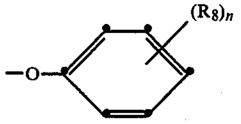

wherein $R_8$ is hydrogen, fluorine or chlorine,

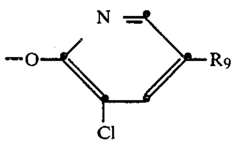

wherein $R_9$ is trifluoromethyl or $—CF_2—CFCl_2$, or

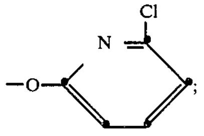

$R_3$ and $R_4$ are each independently hydrogen, fluorine, chlorine, trifluoromethyl or methyl;
U, Z and W are hydrogen;
X is fluorine or chlorine; and
Y is hydrogen, fluorine or chlorine.

4. A compound of formula I according to claim 1, wherein
$R_1$ is chlorine or trifluoromethyl;
$R_2$ is chlorine, trifluoromethyl, trifluoromethoxy, $—O—CF_2—CHF_2$ or the group

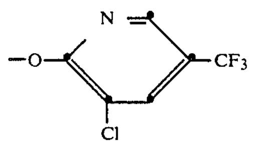

$R_3$ is hydrogen, chlorine or $—CO—OCH_3$;
$R_4$ is hydrogen;
U, Z and W are hydrogen;
X is fluorine or chlorine; and
Y is hydrogen or fluorine.

5. A compound according to claim 1 of the formula

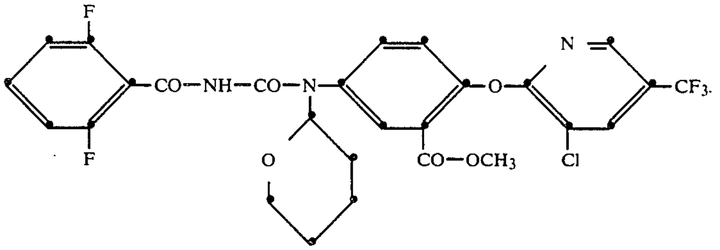

6. A compound according to claim 1 of the formula

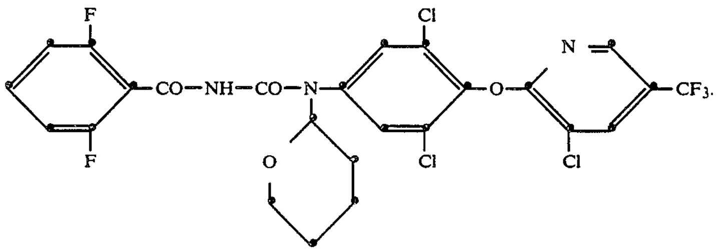

7. A compound according to claim 1 of the formula

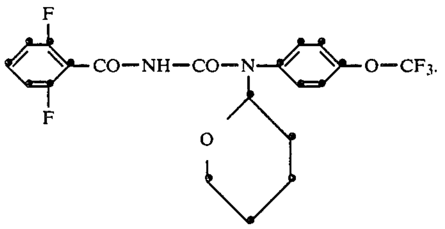

8. A presticidal composition which contains, as active ingredient, a compound according to claim 1, together with suitable carriers and/or other adjuvants.

9. A method of controlling insects and representatives of the order Acarina, which method comprises treating said pests and/or the locus thereof with a pesticidally effective amount of a compound according to claim 1 or of a composition containing such a compound.

* * * * *